United States Patent
Proll et al.

(10) Patent No.: US 9,733,063 B2
(45) Date of Patent: Aug. 15, 2017

(54) METHOD AND DEVICE FOR DETERMINING OPTICAL PROPERTIES BY SIMULTANEOUS MEASUREMENT OF INTENSITIES AT THIN LAYERS USING LIGHT OF SEVERAL WAVELENGTHS

(75) Inventors: Günther Proll, Denkendorf (DE); Florian Pröll, Mannheim (DE)

(73) Assignee: Biametrics GmbH, Tuebingen (DE)

( * ) Notice: Subject to any disclaimer, the term of this patent is extended or adjusted under 35 U.S.C. 154(b) by 138 days.

(21) Appl. No.: 13/982,896

(22) PCT Filed: Jan. 31, 2011

(86) PCT No.: PCT/EP2011/000419
§ 371 (c)(1),
(2), (4) Date: Jul. 31, 2013

(87) PCT Pub. No.: WO2012/103897
PCT Pub. Date: Aug. 9, 2012

(65) Prior Publication Data
US 2013/0314712 A1    Nov. 28, 2013

(51) Int. Cl.
*G01B 9/02* (2006.01)
*G01N 21/45* (2006.01)
*G01N 21/84* (2006.01)

(52) U.S. Cl.
CPC .......... *G01B 9/02* (2013.01); *G01B 9/02024* (2013.01); *G01N 21/45* (2013.01); *G01N 21/8422* (2013.01)

(58) Field of Classification Search
CPC ............ G01B 9/02083; G01B 9/02088; G01B 11/0625; G01B 11/0633; G01B 11/0675;
(Continued)

(56) References Cited

U.S. PATENT DOCUMENTS 5,220,403 A * 6/1993 Batchelder ......... G01N 21/9505
250/358.1
5,563,707 A   10/1996 Prass et al.
(Continued)

FOREIGN PATENT DOCUMENTS

EP    0 598 341 A1    3/2009
WO    WO 97/40366    10/1997
(Continued)

OTHER PUBLICATIONS

International Search Report for PCT/EP2011/000419 issued on Mar. 11, 2011.

*Primary Examiner* — Hina F Ayub
(74) *Attorney, Agent, or Firm* — Muncy, Geissler, Olds & Lowe, P.C.

(57) ABSTRACT

In a method for determining optical properties by measuring intensities at a thin layer, light is directed into the thin layer and passes through a beam splitter, which directs a first part of the light onto the thin layer and a second part of the light onto a reference detector. Interference of the first part of the light in the thin layer is detected via a high-resolution detector and forwarded to an evaluating unit, which determines the reflection and/or transmission coefficients, which are correlated with the optical layer thickness through a comparison using at least one database stored in the evaluating unit. The optical layer thickness is obtained as a gray value modification by way of a gray scale value analysis and a conversion factor stored in the at least one data base. A corresponding device and intended uses of the method and device are also described.

12 Claims, 1 Drawing Sheet

(58) Field of Classification Search
CPC .... G01B 11/026; G01B 11/0209; G01B 11/06
USPC ................................................. 356/503, 514
See application file for complete search history.

(56) References Cited

U.S. PATENT DOCUMENTS

| | | | |
|---|---|---|---|
| 5,999,262 | A | 12/1999 | Dobschal et al. |
| 6,049,506 | A * | 4/2000 | White .............. G01D 5/35303 250/227.19 |
| 6,075,880 | A * | 6/2000 | Kollhof .............. G01N 21/8851 382/141 |
| 6,236,459 | B1 * | 5/2001 | Negahdaripour et al. .... 356/496 |
| 6,248,988 | B1 | 6/2001 | Krantz |
| 6,624,415 | B1 * | 9/2003 | Hattori ................... G01T 1/169 250/336.1 |
| 7,391,520 | B2 * | 6/2008 | Zhou ..................... A61B 3/102 356/479 |
| 2007/0046953 | A1 * | 3/2007 | De Groot et al. ............ 356/512 |
| 2010/0185314 | A1 * | 7/2010 | Xu et al. ....................... 700/109 |
| 2010/0297671 | A1 | 11/2010 | Tschmelak et al. |
| 2012/0052597 | A1 | 3/2012 | Landgraf et al. |
| 2012/0058569 | A1 | 3/2012 | Landgraf et al. |
| 2012/0075464 | A1 * | 3/2012 | Derenne .............. A61B 5/0013 348/135 |

FOREIGN PATENT DOCUMENTS

| | | | |
|---|---|---|---|
| WO | WO 2006/131225 | A1 | 12/2006 |
| WO | WO 2008/067528 | A2 | 6/2008 |
| WO | WO 2010/127834 | A1 | 11/2010 |
| WO | WO 2010/127843 | A2 | 11/2010 |

* cited by examiner

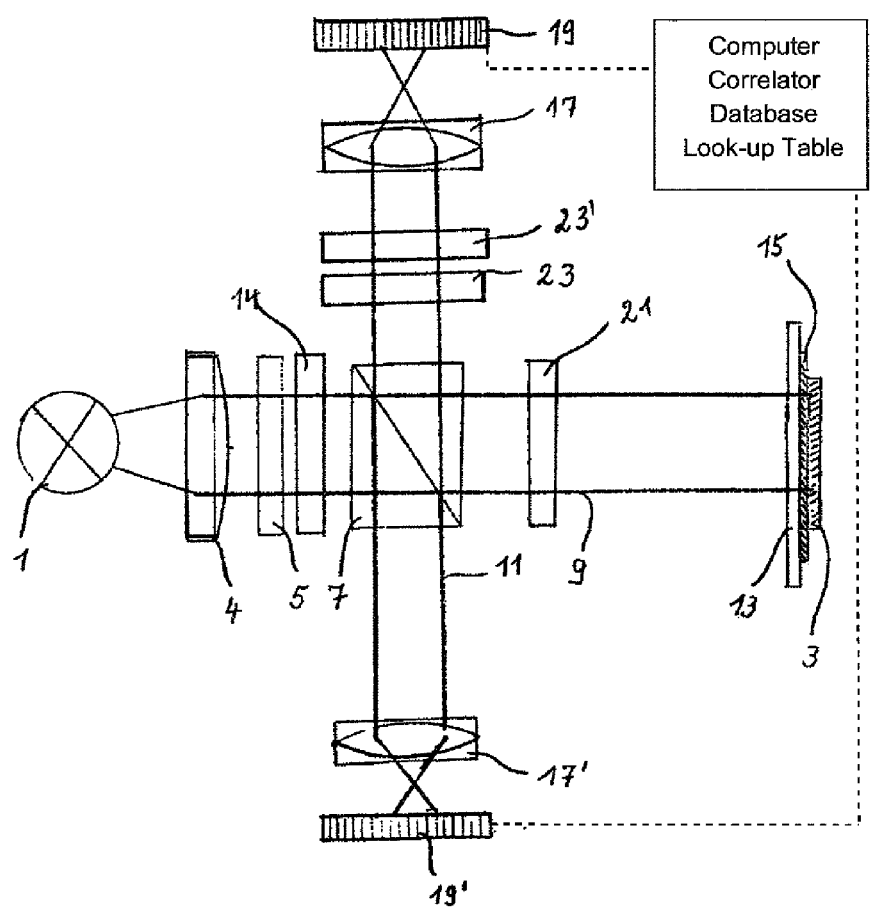

METHOD AND DEVICE FOR DETERMINING OPTICAL PROPERTIES BY SIMULTANEOUS MEASUREMENT OF INTENSITIES AT THIN LAYERS USING LIGHT OF SEVERAL WAVELENGTHS

CROSS-REFERENCES TO RELATED APPLICATIONS

This application is the U.S. National Stage of International Application No. PCT/EP2011/000419, filed Jan. 31, 2011, which designated the United States and has been published as International Publication No. WO 2012/103897, pursuant to 35 U.S.C. 119(a)-(d).

BACKGROUND OF THE INVENTION

The invention relates to a method and a device for determining optical properties by measuring intensities at a thin layer for the detection of chemical, biochemical, medical and/or physical reactions, binding and/or accretion processes as well as other interactions, as preferred uses, in particular in the field of homeland security.

It is known that one can determine physical, chemical, biochemical or biological processes such as reactions, binding and accretion processes and other forms of interaction, at a thin layer of at least partially optically transparent material, by changing the optical layer thickness. For this, light of at least one specific, selected wavelength is radiated onto the sample that is to be examined, which is bound to the thin layer. Interference phenomena are used to determine changes in the optical layer thickness, caused for example by the way a substance that is to be examined reacts with the thin layer that has been subject to an appropriate pre-treatment.

The measurements can be made with the aid of appropriate markers, such as fluorescent markers. More recently, however, they can now also be carried out without markers, and time- and space-resolved.

For the irradiated light, either a single wavelength or several, spectrally separated and thus individual different wavelengths, are radiated onto the thin layers to be examined, and are measured.

Changes in the optical layer thickness are calculated by the spectral location of the interference extrema and their separations from each other. The aim is to observe a shift in the interference pattern. The optical layer thickness can also be determined from the change of intensity at one or more wavelengths. To do this, in prior art one chooses the optimal wavelengths likely to cause the maximum change in light intensity.

WO 2008/067528 A2 D1 describes a so-called "imaging system" at the molecular level, based on the principle of interferometry. Here the analytes in a sample are determined using a measurement assembly which features a light source and a detector for the image capture in the form of a pixel array detector, PAD, with a large number of image elements, so that the irradiated light can be captured and displayed with a good spatial resolution. A biolayer reacts with the analytes that are to be identified, when the sample that is to be examined is brought in contact with it. This biolayer is anchored on a substrate which can convert a phase modulation into an intensity modulation, so that the intensity modulation can then be recorded and displayed directly via the pixel matrix. In addition, a reference surface is provided. First the biolayer is irradiated and the light reflected from the biolayer is forwarded to the pixel matrix, where an image of the sample is produced. Using a so-called image switching unit, which can be a mirror, firstly light is radiated onto the biolayer, and secondly the irradiated light is guided to the reference surface. To do this the mirror is moved accordingly. The light reflected from the reference surface is also forwarded and imaged as the reference image. Using a computer evaluation unit the image of the sample and the reference image are then superimposed. Instead of the mirror the alternating irradiation of the biolayer and the reference layer can also be done using a fast-spinning disk or a polarizing beam splitter.

EP 0 598 341 A1 discloses one or more sensors for the measurement of gaseous and liquid components. The respective optical sensor has a thin film which reacts with the particles to be measured. The measurement is performed via a reflection that is enhanced by interference. The basis for the measurement is the change in layer thickness at the thin film and/or the change in refractive index. The change in intensity of the reflected light is used as the parameter for measurement. If several such sensors are used, they are intended to record various different chemical compounds.

The known methods are very sensitive to intensity variations in the light radiated onto the thin layer. A disadvantage with all previously used methods is that the system technology on which they are based is characterized by a considerable dependence on the intensity. The measuring results in the known methods are directly dependent on the intensity measurements at the region(s) of the thin layer, where changes in the layer thickness were at least partially caused by the interaction with a sample. Because only very small changes in intensity are to be measured here, the measurement of the intensity can be distorted by changes in brightness of the light source. Therefore intensity fluctuations in the region of the incident light have a direct effect on the quality of the measurement results.

The fact that no uniform distribution of intensity could be achieved also had an adverse effect on the reference measurements for the brightness of the light source, at least for such measurements that are to be carried out using so-called multiwell plates. Thus for example for a standard multiwell plate with 96 floors a large common light source in combination with large lenses was used to properly irradiate the multiwell plate, in particular the 96 floors of the multiwell plate. Here it was found that the quality of the light was only sufficient in the central part of the light field emitted by the light source. Therefore the sensitivity and the reliability of these methods of measurement were still inadequate, making it difficult to use the methods in practice.

Basically, the measuring setup for performing such interference measurements consists of a light source, which can be either a xenon high-pressure lamp or an LED (light-emitting diode or a superluminescent diode), a planar carrier, one surface of which is specially activated and pre-treated, and at which the changes in the optical layer thickness are measured, as well as a detector, and an evaluating device In addition to other disclosures, a technique in prior art is known from WO-A-2006/131225 which describes the details of preparing the planar carrier for performing the interference measurements.

Another technique known in prior art is to be mentioned, in connection with the detection of physical, chemical and/or biochemical reactions and interactions at and/or in samples, where the samples are arranged in a planar shape on a substrate plate that has a carrier layer on a carrier plate. The samples are either irradiated with light of various different wavelengths from a variable frequency light source, or a polychromatic light source is used which is fitted downstream with a scanning monochromator. The irradiation of the light is thus always done in sequence, one wavelength at a time.

The portion of the reflected beam coming off at least one boundary layer surface of every single sample, or the portions of the beam or interference that are reflected off and interfering together at the boundary layer surfaces arrayed one behind the other in the direction of the light, are displayed by optical elements in a space-resolving, planar detector array or a video camera. In particular, WO-A-97/40366 discloses an arrangement that includes a plurality of discrete, photoelectric receivers in the form of CCD elements, which are arranged in a matrix-like pattern and thus provide a spatially resolved planar detector arrangement.

This prior art always involves a selective-wavelength detection of the reflected radiation intensities or intensities of the imaged interference effects affected by the samples, i.e. the detection of a spectrum of wavelengths allocated to each sample, and the resulting derivation of parameters that characterize the interactions and reactions to be investigated, is carried out separately and successively for each wavelength. This requires a great deal of work for the evaluation and a correspondingly large amount of time to derive the desired parameters.

All the measurement setups where the detection of the associated wavelength spectrum of a sample, and the resulting derivation of parameters characterizing the interactions and reactions to be investigated, is done separately and successively for each wavelength, have in common that they entail significant computing work to calculate the changes in layer thickness and the underlying concentration levels. The computational complexity is associated with a significant computing time, which makes an evaluation in real time for many samples that are to be analyzed simultaneously very demanding or indeed no longer technically feasible.

In order to achieve a much faster evaluation combined with a more precise determination of the optical properties in the measurement procedure, which thus allows automated measurements and is suitable for routine measurements, PCT/EP2010/002752 proposes a modified method and a corresponding measuring device. In this method, the determination of the wavelength spectrum associated with each sample and the resulting derivation of parameters characterizing the interactions and reactions to be investigated, is not done separately and successively for each wavelength. Instead, light of a narrow-band spectrum is radiated onto the sample and also evaluated as such, as a whole. The detection of the reflected radiation intensities affected by the samples, or the intensities of the imaged interference patterns, is therefore done using a band of wavelengths. This also means that no direct detection of a wavelength spectrum associated with each sample as a function of only one wavelength is made. Instead all the data are available in combination with at least one lookup table, so that it is possible to call up the information about the optical behavior at one wavelength, and the evaluation can actually be made on the basis of the irradiated narrowband spectrum. In this way the method disclosed in the said PCT application can provide a quick and accurate determination of optical properties at thin layers, which allows an automated measurement and is therefore also suitable for routine use.

However, according to PCT/EP2010/002752 this is only achieved by using a special measuring setup, which depends on the type of light radiated on the carrier bearing the thin layer. So according to PCT/EP2010/002752 the light must be radiated directly onto the carrier. With this direct radiation one cannot use a beam splitter to divert some of the radiated light to be used as a reference.

Starting from this prior art, the present invention therefore had the basic aim of further developing the method and the device presented in PCT/EP2010/002752 so as to allow a quick, automated measurement and thus a routine use, and to ensure that its design for the irradiation of light does not depend on the light being radiated directly onto the carrier plate with the restrictive measures that entails.

SUMMARY OF THE INVENTION

This object is attained by a method for determining optical properties by the measuring intensities at a thin layer, where light in the form of more than one wavelength at the same time is radiated into the thin layer via coupling elements, said thin layer having previously been applied to an at least partially transparent carrier. Here the light can be irradiated in the form of a narrow wavelength range or light of a wide wavelength range can be irradiated and reduced to a desired narrow wavelength range by the positioning of filters. The light that has been reduced to the narrow wavelength range in this way first passes through a beam splitter, which directs a portion of the light onto the thin layer, and a further portion of the light onto a high-resolution reference detector, which measures the intensity of the incident light at each given moment. Interference effects at the at least one thin layer are simultaneously recorded throughout the whole narrow wavelength range by a high-resolution detector, and the signals recorded by the detector and the reference detector are forwarded to an evaluation unit, which determines the reflection and/or transmission coefficients for each image point on the thin layer, regardless of the intensity of the irradiated light. It does this by simultaneously displaying all quotients from the signals received from the detector and from the reference detector for each wavelength of the narrow wavelength range; while correlating these quotients with the optical layer thickness at every measured image point for the qualitative and/or quantitative determination of the optical property, by means of a comparison using at least one database stored in the evaluation unit; the said database containing all the data, in particular in the form of calibration tables, for mapping each measurement result to a quantitative result, so that the optical layer thickness is obtained by way of a gray scale value analysis and a conversion factor stored in the at least one database as a gray scale value modification.

Therefore in this manner in the invention the relative intensity and thus the reflection coefficient for each image point, i.e. every pixel of the thin layer imaged in high-resolution, are obtained by means of the high resolution detector and the similarly high resolution reference detector. Here for the first time in the context of determination of optical properties by measuring intensities at a thin layer, a change in the optical layer thickness is detected accurately and quickly by means of a gray scale value analysis.

The gray scale value analysis here is to be taken to mean a surface testing procedure in the broadest sense, in which gray scale values of images (per pixel) are measured and compared to an index value. The index value is derived from a reference measurement and/or stored in the database.

The use of a gray scale value analysis in this analytical area is based on the principle that each pixel of the CCD camera can be correlated to a region on the thin layer, that is to say to a place on the array used for the respective examination.

From the respective, specific optical layer thickness the concentration of the analytes can then be determined and, if necessary, corrected using the correction value from the reference regions. This results in a determination method that is not only fast but also very precise.

If, according to another preferred embodiment, the measured concentration value is additionally compared to reference concentration regions, this allows one to draw diagnostic conclusions.

In addition to the determined measured values, all the other required data is stored in the database(s)/lookup table(s) or calibration table(s).

Here the reflection coefficient is determined as the ratio of the amplitudes of the incident and reflected light wave, where the reference detector merely has the task of measuring the current illumination intensity, so that fluctuations in intensity of the irradiated light can be balanced out, and the value obtained when determining the layer thickness in this way is independent of the incident light intensity.

The ratio of the amplitude of the reflected or transmitted light to the amplitude of the incident light wave can be determined from the corresponding reflection or transmission factors by using the Fresnel formulas, which in turn are derived from the Maxwell equations. The reflection coefficient R is based on the ratio of reflected power to incident power, and the transmission coefficient T is based on the ratio of transmitted power to incident power. These principles are widely known, but not their application to the determination of optical layer thicknesses.

In this manner the intensity of one, two or more superposition waves can be measured.

The evaluation unit may be fitted with a comparator and an associated database in the form of at least one lookup table, so that the conversion factor(s) for the gray scale value analysis are stored in the lookup table. The other data required, in addition to the determined measured values, for carrying out the gray scale value analysis and, where appropriate, the comparison with reference concentration regions, and other parameters, can all be stored in the lookup table.

In this way the measured concentrations can for example be matched to the correction value from the reference regions and corrected.

Comparators for processing digital signals are generally known, even though for quite different applications.

One can for example radiate light that is already narrow-band e.g. from a light-emitting diode, or one can radiate light of a wide wavelength range and reduce it to a desired narrow-band wavelength range by means of filter arrangements.

The narrow-band wavelength range can be chosen in such a way that it has wavelengths with both the expected intensity maxima and minima for the measurements.

The desired parameters to be determined from the measurements are derived from the change in the detected light intensity. If for this purpose measurements are made in least two wavelengths, for example in narrow-band wavelength ranges, then according to the invention wavelengths with both expected intensity maxima and with intensity minima can be selected. This means that in contrast to the previously known principle of reflectometric interference spectroscopy, measurements are also made at such wavelengths where nothing actually happens. The parameters to be determined are then obtained from the relative comparison with such wavelengths that produce or are at least expected to produce intensity maxima.

For the purposes of the present invention the term narrow-band wavelength range is defined by the wavelength range inherent in a narrow-band light-emitting diode.

It well known in prior art that light-emitting diodes (LEDs) always emit a narrow limited wavelength band due to the way they are designed. For light-emitting diodes the spectral full width at half maximum is typically between 20 and 35 nm. This half width is also used as a tolerance range for the purpose of the present invention.

Furthermore, the thin layer on the carrier can be applied over the whole surface or in the form of several partial regions, the multi-spots, or a multiwell plate can be used, where has the thin layer in each well of the plate, without departing from or substantially changing the inventive principle for determining optical properties.

To determine the optical properties by measuring intensities at a subdivided thin layer (multi-spots), which are arranged on carrier that is at least partially transparent, the light in the narrow wavelength range is radiated onto at least a part of the layer regions. The layer regions, i.e. the spots, each have at least two boundary surfaces, where the wave fields overlap to form a superposition field, so that the interference can be measured at each of these layer regions and forwarded to the detector.

Because high resolution detectors, such as CCD cameras, are used, each of the measurements can generally be carried out space- and time-resolved.

When using this multi-spot method, regions can be entered in the database(s) or in the lookup table that allow the mapping of specific spots and reference areas.

Now the said change in gray scale value, which corresponds to a concentration of analyte, can be combined with an additional stored calibration; and then regions can be entered and specified in the database(s) or the lookup table that enable a mapping of certain spots and reference areas. This then allows one to calculate the concentrations very precisely, and to make reliable diagnostic statements by comparing with reference concentrations.

The thin layer can have reactive elements, which may be, for example, various biomolecules, such as antibodies, which then react with the corresponding species in the sample to be tested, which can for example be antigens. When using microtiter plates or flat carriers fitted with the reactive elements using the multi-sport method, such as slides, several different reactive elements can be provided. The optical layer thickness changes as the species of the sample to be tested that correspond to the respective reactive elements are deposited.

Basically, when the light is radiated onto one of the aforesaid carriers, which bears the thin layer with the reactive element(s), the incident light field produces a superposition field that causes the interference effects on which the measuring principle is essentially based. Here a boundary surface is formed by the thin layer or by the regions of the thin layer, either on the flat carrier or in the wells of the microtiter plate, in the direction towards the carrier and at the boundary pointing away from it, where overlapping wave fields produce a superposition field, which is forwarded to the detector. The carrier itself is unimportant here and, provided it is at least partly transparent, may be selected as desired.

The intensity of both the resulting reflected light field and transmitted light field depends on the thickness of the thin layer. There are other additional factors that are also involved in producing the result, e.g. the refractive index of the thin layer.

Reactive elements in the context of the present invention may also be nanoparticles of any type, so the new measurement method is generally a measurement method applied at boundary surfaces. The quantity of interest is reduced to the distance between the boundary surfaces.

This extension of use is possible because the dependence of the measurement result on the light intensity is eliminated by forming the quotients.

If light is radiated onto an at least partially transparent carrier, a light source of a specific light intensity is required. It is important to measure this light intensity, which is done using the reference detector, and also the intensity of the at least one reflected or transmitted superposition wave from the thin layer on the carrier. When the quotient is now formed from these two values, in the evaluation unit by using the comparator, the reflection or transmission coefficient is obtained, as briefly described in a general way above, and thus the measuring signal that is actually processed. If this measurement signal is now correlated with at least one database stored in the evaluation unit, this allocation of the measuring result or all the measuring results leads to the desired quantitative result. For this the database contains all the data essential for the evaluation, in particular in the form of calibration tables.

The inventive measurement method that is based on the determination of reflection or transmission coefficients allows one to significantly speed up the evaluation of the measurement results. The data required for compensation can now be stored in a calibration table, commonly also referred to as lookup tables.

A lookup table in the context of the present invention refers to a data structure or database that is prepared and stored using a computer medium. This makes it possible to quickly determine and match the measured values by using the quotient determination prepared beforehand in the form of tables in reflection or transmission. Furthermore, other necessary or useful data for the evaluation are stored in the form of the lookup table. This also includes the known intensity distribution for a specific wavelength of the lamp that is used. Finally all the information for the evaluation, concerning the sample, the thin layer, the carrier and the irradiated light at each of the wavelengths used, is stored in the lookup table or database and ready for retrieving. One advantage that such lookup tables provide is rapid matching, which is particularly required for routine tests.

Indeed this also is especially favorable in the way it ensures that for different arrangements or multiple arrangements of the reactive elements on the planar carrier or on the floors of the multiwell plate, e.g. in the form of specified patterns, a reflection or transmission coefficient can be specified for each individual region of the reactive elements, so that a reflection or transmission coefficient can be associated with each region of the reactive elements. Because the effect of intensity fluctuations in the incident light and hence the intensity of the incident light field is eliminated in favor of the only important change of the reflectivity or transmissivity of the superposition wave(s), the noise caused by the intensity variations of the light source which had previously had such an adverse effect on the quality of the measurements is avoided. It is now possible to achieve a resolution that is orders of magnitude better than was previously possible in prior art.

While it was necessary in prior art to evaluate light of a single wavelength or of several individual wavelengths, and the evaluation for each single wavelength had to be performed separately, by using the invention it is possible to radiate the light of a narrow-band wavelength spectrum onto the carrier and perform the evaluation together.

The inventive method is performed without markers, that is to say markers, such as fluorescent markers, are not required.

According to a particular embodiment of the method of the invention, the optical properties are measured by measuring intensities on a thin layer that is divided into several partial regions arranged on the at least partially transparent carrier. Such partial regions are known as multi-spots. Here light of at least one narrow wavelength range is radiated onto at least part of the partial layer regions. These layer partial regions each have at least two boundary surfaces where the wave fields are superimposed, creating a superposition field. In this way the interference effects can be measured at each of the layer regions as relative intensities of at least one respective superposition wave, and each transmitted to at least one detector. In addition, the intensity of the spatially incident light is also first measured on at least a portion of these coated partial regions or multi-spots, with an intensity sensor associated specifically with this partial region.

The invention also relates to a device for determining optical properties by measuring intensities at a thin layer, with at least one light source, which emits light of more than one wavelength, at least one optical coupling element, an at least partially transparent carrier, which has a thin layer for the determination of the optical properties either covering its whole surface or parts of it; at least one optical medium to radiate the light from the light source into the thin layer, and to direct a part of the light unchanged to a high-resolution detector, and also to direct the light reflected from the thin layer by multiple reflection, which can if required be modified by a sample that is to be examined; and with an evaluation unit that is downstream of the detector and the reference detector, which contains a database for comparing the measured values with previously known data and distribution functions for applying a gray scale value analysis, in order to determine the desired optical property by means of correlation with a respective conversion factor.

While such gray scale value analyses are basically already known, their use in the context of spectroscopic procedures or in the context of the determination of optical properties by measuring intensities at a thin layer was previously not possible.

Because this is now possible using this invention, the measurement and evaluation are significantly speeded up and now for the first time a reliable practical application is provided to determine optical properties by measuring intensities at a thin layer.

For this the gray scale value correlation analysis as a standardized gray scale value correlation is available to determine an absolute quality standard.

The gray scale value correlation enables a pixel and grid evaluation as an image analysis by gray scale value correlation, and therefore a contact-free planar determination.

Here one can refer to the comparison with a bitmap, where the recorded images are matched against reference images that were taken earlier and stored in a kind of database, and where values could be assigned for example by using a vector comparison, also by using light-dark transitions (contrast levels).

Of interest is the histogram analysis, where gray scale value histograms of images or image areas are calculated, gray scale value distributions are determined, and desired parameters, such as diagnostic statements, are determined by comparison with (stored) previous information from reference measurements.

In this way, for example, differential histograms of images and image areas are calculated and assessed by reference to previous information defined by precisely predetermined, stored parameters.

In contrast to the conventional measurement setups for determining optical properties, including, for example, measurement assemblies in the area of reflectometric interference spectroscopy (RIfS), the inventive device requires no coupling prisms or optical coupling liquids of the type used in prior art to prevent disturbing reflections. Nor does the inventive measuring principle require the use of a monochromator. It is instead of special importance to use more than one wavelength as basis for the measurement and evaluation. This does not preclude collimator arrangements to produce a parallel beam, and other optical coupling elements in the path of the measuring beam, that serve to direct the light of the at least one narrow wavelength range onto the thin layer.

In this context it is to be stated that one does not have to use a wedge-shaped carrier plate as disclosed, for example, in WO-A-97/40366 as a possible embodiment, or prism couplers for the light.

The inventive device makes it possible to measure the relative intensity within a narrow wavelength range and, based on this relative intensity, to infer the respective layer thickness of the thin layer, which may have changed by interacting with the species of a sample to be tested. It should be noted here that the thin layer specially prepared for the said interaction may also be prepared so that it does not react over its whole surface with the sample to be tested, but only in selected partial regions. Furthermore, specified partial regions of the thin layer may undergo a different sample preparation, thereby allowing an analysis of different species in a sample.

Generally the preparation of a carrier, such as used for example in the field of reflectometric interference spectroscopy, has been amply described in patents and in the technical literature and is therefore known to the expert, and reference is made here to the entire contents of that patent and technical literature.

According to one embodiment a large surface area light source can be used, preferably in the form of a high-power light emitting diode or a laser diode, which is paired with at least one wavelength filter to select a narrow-band wavelength range. This allows one to make rapid measurements of spatially recorded intensities.

The at least one light source is preferably not directly connected with the carrier that bears the thin layer. This avoids having to discard the light source along with the carrier. The same applies to the detector arrangement.

The reflection caused by the employed light source is to be detected or recorded as an intensity, where the term "record" is to be understood in its broadest sense.

According to the invention, the sensor used for such recording can be configured as a one-dimensional or a two-dimensional CCD sensor.

The light sensitivity of such CCD sensors is known. The signal produced by them is directly proportional to the incident light. If one-dimensional CCD sensors are used operating as so-called line sensors, they are referred to in the context of the present invention as CCD arrays in accordance with the commonly used technical designation.

When using two-dimensional CCD sensors, these are also referred to as CCD image sensors in accordance with the commonly used technical designation. According to the invention, two-dimensional CCD sensors constructed as a matrix of light-sensitive photodiodes or pixels are used.

Especially preferred here is to use such CCD image sensors that ensure a balanced relationship between the sensitivity to light and dynamic range of the sensor, defined across its pixel area, and the image resolution which is known to be inversely proportional to the sensitivity to light.

In addition, a suitable coupling between light sources and the light sensors ensures that the blooming effect, and thus the bleeding of charge due to overexposure, cannot develop. This means that one can preferably avoid having to use a so-called "anti-blooming gate", which could lead to a non-linearity between the incident and detected light and the associated signal assigned, depending on the selected exposure times and thus depending on the samples to be tested.

Similar considerations, where applicable, apply to the CCD arrays as well.

When using CCD image sensors, according to a preferred embodiment these are used in the form of a planar camera system, that allows an optical imaging of the chemical compounds disposed on or coupled with the thin layer, for example arranged as spots. This camera system is preferably constructed in the aforementioned digital form, and basically provides a complete image of the compounds in the thin layer, whether they be arranged across an area or in spots, via the pixels.

The use of CCD arrays is preferred if a structured, spatially resolved detection of the reflected light rays is to be made in such a way that there results a direct mapping of the light radiated onto the carrier with the thin layer in the form of multiple individual light sources, to each individual irradiated spot on the thin layer. This is especially beneficial when there are various different compounds disposed on the thin layer or coupled to it. It allows the selective detection of the different components in the sample to be analyzed.

In this way a number of signals are recorded, each originating from the individual spots on the thin layer illuminated by the light source. Then no actual pattern recognition is necessary, the amount of data is significantly reduced and the signal quality is thereby improved.

The carrier itself can be arbitrarily selected. This applies to the material and the shape, provided the carrier has at least partially transparent areas used for the analysis, i.e. to determine the intensity levels. For example the carrier can be in the form of a flat, two-dimensional carrier or a carrier in the form of a microtiter plate. The thin layer is then formed in each of the wells of the microtiter plate. Suitable carriers and carrier materials are sufficiently known to the expert, for example from the field of reflectometric interference spectroscopy.

In particular, but not exclusively, if the carrier is a microtiter plate, the device for determining optical properties by measuring intensities can be constructed in a particular embodiment for measurements on a thin layer divided into several partial regions, the so-called multi-spots. To do this, the inventive device has at least one light source which emits light of at least one narrow wavelength range, that is directly adjusted for an at least partially transparent carrier which has the said layer regions. The at least one light source irradiates the respective partial region of the layer. At least one detector is provided, which operates together with at least one reference detector. Each of the partial regions of the layer has at least two boundary surfaces, where superimposed wave fields produce a super-position field, which is to be transmitted to the at least one detector. At least one part of the coated partial regions is associated with at least one intensity sensor for determining the intensity of the light spatially incident on the partial region.

In addition the invention also relates to the use of the device for determining optical properties by measuring intensities on a thin layer, as described above, and the likewise aforedescribed method for the detection of chemical, biochemical, medical and/or physical reactions, binding and/or accretion processes, and other interactions. Preferably, this application relates to homeland security.

BRIEF DESCRIPTION OF THE DRAWING

In the following, the invention will be described in more detail by using an example embodiment, its modifications, and the accompanying drawing.

It is shown in:

FIG. 1: a schematic diagram of an inventive experimental setup with a planar carrier and various filters for the measurement using reflection;

DETAILED DESCRIPTION OF PREFERRED EMBODIMENTS

In FIG. 1, as the only FIGURE, the reference number 1 indicates a light source in the form of an LED light, by means of which a sample 3 to be tested is irradiated vertically. Before this, the light emitted from the LED light passes through a diffuser 4 in the form of a filter, which distributes the light evenly, and a polarizer 5 to produce linearly polarized light. In this way, light of a narrow wavelength range defined by the LED lamp is directed onto the sample 3, by also passing through a polarizing beam splitter 7. The beam splitter 7 divides the light into a measuring beam 9 and a reference beam 11. This test arrangement also allows one to use a classic broadband light source, and to produce the desired narrow wavelength range by using a downstream wavelength filter. Such an optional wavelength filter is provided in FIG. 1 for the purpose of illustration and is indicated there by reference number 14.

The sample 3 contains an at least partially transparent carrier 13, which in this example embodiment is made of glass in the form of a glass slide, and on which a thin layer 15 is applied. To apply this thin layer 15, the designated surface of the carrier 13 is first activated by producing OH groups on the glass surface.

The glass surface is now prepared for a surface treatment in the form of silanization with epoxy groups, which in this case is performed with an epoxy silane in the form of 3-(glycidyloxypropyl) trimethoxysilane (GOPTS), where this is only one of many possible compounds for silanization that is given here as an example. Following the silanization, a reaction with a biopolymer, such as polyethylene glycol (PEG) of a suitable chain length, is then performed. It is also possible to use at least two different PEGs each with different chain lengths. Only then are selected, specific capture molecules immobilized with the biopolymer, which completes the preparation of the thin layer for the detection of the desired species in the sample to be investigated.

This formation and preparation of the thin layer 15 is only briefly outlined for the purpose of the present invention, because an expert will find more precise details in prior art, to which reference is made here in full. The description of the present invention is not concerned with the formation of the thin layer 15, but rather the analytical side of light irradiation, detection and processing of the resulting signals.

The thin layer 15 is affected by the sample 3 to be tested, because the interaction of the capture molecules on the thin layer 15 with the corresponding species in the sample causes a change in layer thickness in the region of the interaction. This change in layer thickness in turn affects the light that is directed via the measuring beam 9 onto the carrier 13 and reflected off the surface of the thin layer 15; the light then being diverted by the beam splitter 7 and imaged via an imaging system 17 on a detector arrangement 19; where here the detector arrangement 19 consists of a CCD camera.

For the measuring process itself it is important that the light is radiated into the thin layer 15 without it being coupled in the carrier 13. The multiple reflections at the boundary surfaces of the thin layer caused thereby are measured and evaluated. No evanescent field is needed. Due to this fact it is also possible to measure transmission instead of reflection, if desired. Therefore FIG. 1 shows the measurement of the reflected radiation as an example, without excluding the option of measuring the transmitted radiation.

The light of the reference beam 11is unaffected by the sample and is imaged via a separate imaging system 17' on a detector arrangement 19' serving as reference, in the example embodiment again in the form of a CCD camera. The reference detector 19' serves to measure the current illumination intensity, i.e. of the light source 1 that is used. In this way spatial inhomogeneities caused by fluctuations in intensity of the lamp used as light source 1 are recorded and included in the analysis.

Both detector arrangements 19, 19' are connected to an evaluation unit. This evaluation unit includes a computer system for control, data acquisition and evaluation. This evaluation unit enables, among other things, the corresponding association of the reflection with different locations on the carrier 13, or the thin layer 15. This is important for assays using a carrier 13 that is prepared according to the "multi-spot method", i.e. where the thin layer 15 has specially prepared areas, the spots, within which the capture molecules, optionally also a number of different capture molecules, are applied. It is then possible to investigate, on the individual spots, a range of completely different reactions and interactions with the species in the sample to be tested. In general, this method is suitable for all tests of biomolecular interactions. Moreover the tests can be performed in a range of very different ways.

From the type of the selected capture molecules it can be determined whether the species present in the sample to be tested interact selectively or non-selectively with the thin layer 15, or only with partial regions of the thin layer (the spots), and thus at least partially cause a change in layer thickness.

The spots distributed over the surface of the carrier 13 can be arranged in a matrix pattern. In this manner one can initiate a spatially resolved interaction with the species of interest in each sample, e.g. with hormones or antibodies, and detect and analyze it accordingly.

When only specific regions of the surface of the carrier 13 have capture molecules, one can differentiate between specific and non-specific binding effects and hence interactions by comparing the detection in these regions with untreated regions of the surface of the carrier 13. The detector arrangement 19 in the form of the high-resolution CCD camera is of essential importance for this. Using the high-resolution. CCD camera, it is possible to carry out measurements at every image point and resolve the entire observable area of the carrier 13 with the spots distributed on it, or the single large spot in the case where the application is done over the whole surface. Here the reflection coefficient is determined for each image point, i.e. for each pixel. As already described above, the reference beam 11 with the reference detector 19' is used to measure the current illumination intensity, i.e. of the light source 1 that is used, in order to record the lamp fluctuation and be able to include it in the evaluation for each image point.

The quality of the data material obtained and its evaluation are of crucial importance for the informative value of such investigations, which are possible in many different ways. For the quality of the evaluation, not only is it important here to have a good signal-to-noise ratio, it is also equally important to be able to use such investigations in a quantitatively meaningful way.

Basically the light from light source 1 is radiated onto the thin layer, which interacts with species of a sample by a targeted coating with biopolymers and capture molecules, either on the layer as a whole or in specific regions of it—the spots,—thereby causing a change of layer thickness, and the superimposed point waves of the incident light each produce a superposition field in transmission and one in reflection. For the purpose of the present invention, it is generally preferred to observe the reflected superposition field. However, one can just as well observe the transmitted superposition field.

For this it is not necessary to use all the types of filters that have been mentioned and that are shown in FIG. 1. For example when using a narrowband light source, one may not have to use the wavelength filter 14. At this point one should stress the importance of the fact that the measurement is performed as a whole across a narrow-band wavelength range, and is then also available as a whole for the purpose of evaluation. This is to be distinguished from the approach in the known prior art, where measurements are only made selectively one wavelength at a time. This means the evaluation of multiple wavelengths was not done simultaneously but successively, which is very time-consuming.

With regard to the filter one should note that the thin layer 15 itself also has filter properties, which according to the inventive measuring method can be exploited by irradiating into the thin layer. In this manner the thin layer itself represents an interference filter.

When a broadband light source is used, the resulting wavelength diagram is broadband. Therefore in this case at least one narrow-band wavelength filter 14 and/or spot filter 21 is used. This makes it possible to measure the reflection in a predetermined narrow wavelength range selectively and wavelength-dependent, without having to already choose the light source 1 itself as narrow band, for example in the form of a light-emitting diode. Accordingly the detector filter(s) 23, 23' are also chosen as narrow band. The corresponding wavelength range is slightly offset as a whole, in relation to the range of the spot filter 21.

From these filter arrangements there results an overlap region where all the filters used are transmissive. According to the invention, this overlap region can now be used to control the quality of the measurement precisely, depending on the particular system to be examined. The broader and larger the overlap region, the greater, too, is the intensity of the light radiated on the detector or the detector arrangement 9. When, for example, the passband curve of the spot filter 21 is changed, while the other filters remain the same, the light intensity detected at the detector arrangement 9 also changes.

For the evaluation itself, several distinct, space- and time-resolved data are obtained using the measurement setup shown. Thus, firstly, information is obtained from the irradiated light in the selected narrow-band wavelength range, by recording the measuring beam 9 as well as the detector arrangement used as reference detector 19'. This can for example provide details about the intensity variations of the lamp at a defined wavelength. Secondly, data is obtained for the sample from regions of the thin layer 15 that are affected by the sample 3 to be tested, as previously described, and where there is a change of layer thickness caused in the region of the interaction, as well as from other regions where no interaction has occurred.

To enable the measurement of a narrow-band wavelength range as a whole, i.e. without the measurement data having to be evaluated wavelength by wavelength and successively in a laborious manner, it is important that the information about the behavior at a certain wavelength in relation to the two kinds of data referred to above, that is to say that of light irradiated at one wavelength and that of the behavior of the thin layer in its free regions, is already stored in the form of a database within the evaluation unit and available for querying. This will be dealt with again later in more detail.

At this point one should still note that the filter arrangements shown in FIG. 1 are entirely optional in nature. The specified measuring principle can be realized in other ways that are evident to the expert, i.e. in such a way that at least some of the said filters can be replaced by other measures.

In what follows we will again present more details of the variant of the carrier coating design where the carrier 13 does not have a thin layer 15 applied over its whole surface, but partial regions applied by a multi-spot process, with the appropriate biopolymers and the capture molecules affixed to them for interacting with the corresponding species of the sample to be tested. Basically the partial regions have at least two boundary surfaces, at which superimposed wave fields arise, that produce the superposition field, which is reflected towards the detector or the detector arrangement 19.

Regarding the light source 1, which serves here to illuminate the partial regions of the thin layer 15, no such restrictions apply to the lighting options as were mentioned for the case where the thin layer 15 is applied over the whole surface, and a broadband light source that is reduced by suitable filters to a desired narrow-band range can be used, or an LED light with the desired narrow-band range can be selected.

The reference detector 19' is again used to measure the current illumination intensity, i.e. of the light source 1 that is used.

In another variant, instead of the previously used carrier 13 with a planar coating or an application in the form of multi-spots, a multiwell or microtiter plate was used.

Here the multiwell or microtiter plate replaces the carrier 13, as shown in FIG. 1, the remaining measuring setup being the same, so that it is not shown again separately.

When using the microtiter plate as carrier 13, the thin layer 15 is applied to its floors, the wells. To apply this thin layer 15, the floors of the wells are first activated in the same way as described above with reference to the carrier surface, by producing OH groups on the floors of the wells.

Then the surface is treated by a silanization with epoxy groups, which is again performed with an epoxysilane in the form of 3-(glycidyloxypropyl) trimethoxysilane (COPTS). Following the silanization, a reaction is performed with a biopolymer, such as polyethylene glycol (PEG) of a suitable chain length. Here again at least two different PEGs of different chain lengths can be used. Only then are selected, specific capture molecules immobilized with the biopolymer, thereby preparing the floors of the wells for detection of the desired species in the sample to be tested.

In this briefly described, commonly known preparation of the floors of the wells, which so far is not substantially different from the preparation of the surface of other carriers 13, in one variant the activation of the floors of the wells and the subsequent treatment were not done over the whole area, but instead only specified regions of the floors of the wells were treated in the aforementioned manner. These defined regions were made in such a way as to form predetermined, well-defined patterns. The subsequent measurement, therefore, was used not only to determine the change in the layer thickness due to interaction between the thin layer and the species to be examined in the sample, but also simultaneously was used to recognize the pattern previously applied to the thin layer, which poses significantly higher demands.

Here patterns can be imprinted and detected on the surface of the floors of the wells in the following regions:
  Patterns when activating the floors of the wells and/or
  Patterns when treating the surface in the form of silanization and/or
  Patterns during the reaction with a biopolymer and/or
  Patterns when immobilizing the selected, specific capture molecules.

The patterns are either applied by activating or silanizing the defined partial regions, or by reaction with the biopolymer, or by immobilizing the capture molecules in defined partial regions, or by transferring the pattern structure formed in a previous step to the next reaction step.

If for example only a defined partial region of the surface of the floors of the wells was activated at the beginning, then only these activated regions can be silanized. So the pattern continues. The pattern formation can equally well be done at the conversion stage of silanization, by applying a mask, by a specific application of multi-spots or the like. The same applies to each of the conversion steps up to the immobilization of the capture molecules.

The pattern formation described here in a simplified manner is used for coding the respective microtiter plate as carrier 13, or likewise for the coding of the respective planar carrier 13, including the "multi-spot" variant, for example to distinguish counterfeit products from genuine products and thus providing quality assurance. This pattern formation and coding as such is not part of the present invention. The present invention is concerned with capturing and evaluating the patterns formed as well as the change in layer thickness caused by the respective observed interaction, at a high standard of quality, and preferably automatically.

Further details about the pattern formation and coding are described in PCT/EP2010/002728, the whole of which is referred to here.

Both the encoding of the planar carrier 3, also when using the "multi-spot" application, and of the microtiter plate, were successfully carried out in a number of tests. The carrier 3 or microtiter plates prepared in this way were then used together with the measurement setup shown in FIG. 1 and described in detail above to determine the optical properties at thin layers. This enables a very fast and also very accurate detection of physical, chemical, biological, and/or biochemical reactions and interactions. Therefore the way is opened up for automated measurement in a manner that will be described in more detail below.

The sample 3 is, for example for the detection of biological and/or biochemical reactions and interactions, preferably a liquid, and for the purpose of conducting experiments in the context of this invention was investigated mainly, but not exclusively, as an aqueous sample. The sample is then, for example, connected to the carrier 13 via a flow-through cell.

The wavelength filter 14, as shown in FIG. 1, can be useful when using a broadband light source 1 in the same way as a narrowband light source 1 in the form of a light-emitting diode.

This wavelength filter can be used in two ways with a broadband light source. It can be used to select the wavelengths to be irradiated on the sample 3 and thus limit the broadband spectrum of the light source 1 to the desired narrower band range, and at the same time it can limit the direction of the light.

It is particularly important for the evaluation technique one which the invention is based that the sample 3 is ultimately illuminated with light of a narrow-band spectrum. This means that the incident light should not have only one wavelength, nor should the light be radiated successively with just a single wavelength at a time.

This is the principle for the expert to consider when deciding whether to use the wavelength filter 14 to limit the direction and/or the wavelengths, based on a selected broadband or narrowband light source 1.

The thin layer 15 is additionally to be understood as an integrated filter. That is to say, it is chosen so that it has filter properties, because its reflectivity depends on the wavelength.

When the light that is selectively reflected in this way is now transmitted towards the detector 19, it first also passes through a first and a second detector filter 23, 23'.

These detector filters 23, 23' can also have a direction-limiting function to improve the measurement result. With the inventive measurement setup a signal can be measured at the detector or the detector arrangement 19, that corresponds to the radiation reflected from the thin layer 15, and that has an extremely favorable signal-to-noise ratio. The relative reflectivity of the thin layer, whether across the whole surface or in partial regions applied using the multi-spot method as well as in the wells of a microtiter plate, can then be measured with extreme precision.

The further processing of the data obtained using an experimental assembly as shown in FIG. 1 shall now be described in detail.

All the data obtained from the detector 19 and the reference detector 19', which is used to record the inhomogeneities caused by fluctuations in intensity of the lamp, are forwarded to a comparator which is coupled to a lookup table 27. This lookup table 27 is a database, which contains all the necessary data about the behavior at a particular wavelength, including an intensity distribution function, which can now be accessed during the computer-aided evaluation.

Thus the intensity distribution function corresponds to a known, specified distribution table of the incident light intensity in the form of a database or lookup table 27 stored in the evaluation unit. The lookup table contains all the data and calibration tables that are required for assigning the obtained space- and time-resolved measurement results to a quantitative finding.

When the detector 19 and the reference detector 19' have forwarded the signals received by them to the comparator 25, the reflection coefficient is formed for each measured image point, i.e. each pixel, of the high resolution CCD cameras used as detectors 19, 19'. The reflection coefficient is independent of the intensity of incident light from the light source 1. The detector 19 in the example embodiment captures the signals of the reflected 3-(glycidyloxypropyl) trimethoxysilane (GOPTS).s as input signals. The input signals of the transmitted superposition wave can also be captured.

Regarding the comparator used in the example embodiment and comparators in general, one should add that they be fast and energy-saving in operation. Comparators are available both in digital technology, to compare digital signals, as well as in analog circuitry. Both types of comparator can be used here. Their particular use in each case depends on the underlying measurement setup.

Using the lookup tables the previously received signals can then be converted directly, without further calculations, into an output signal. The respective processing units in the form of the respective lookup tables stored in the computers can be designed as separate or combined together.

During the signal processing, spatial dependencies can also be taken into account. This too is done via a calibration table or lookup table, that is likewise stored in the computer(s) of the evaluation unit.

The data processing is performed by using a gray scale value analysis. For this, conversion factors are stored in a database or the lookup table, to obtain the value in nm for the optical layer thickness that corresponds to the change in gray scale value. And for this it is also necessary to use the database to find the correlation between a pixel of the CCD camera and the location on the thin layer to be examined, i.e. on the array. For example when applying the multi-spot method, regions can be stored in this way as tables in the database/look up table, which allow the precise mapping of specific spots and reference regions.

By using such a database one can allocate diagnostic parameters to the spots or the thin layer or its partial regions. Thus a change in gray scale value will now correspond to a certain concentration of analyte. This change in gray scale value is now combined with another stored calibration, and also correlated with the regions stored in the database, which allow the mapping to the spots, the thin layer or partial regions of the thin layer. From these correlations, the concentrations can be calculated quickly with great precision. Additionally, in some measurement runs a correction of the detected concentrations was also performed by using a correction value from the reference regions. Furthermore, in special, selected test runs each of the detected concentration values was compared with reference concentration regions, thus allowing one to obtain diagnostic findings.

In particular the gray scale value analysis and the gray scale value correlation analysis have proved to be suitable procedures.

In the inventive signal processing the temporally variable course of the measured intensity of light radiated from the light source 1 is measured using the reference detector 19', and the superposition field is measured in reflection by the detector 19. The measurement can also be performed in transmission.

Here the reflection is generally weaker than the transmission. Both curves vary in proportion to the intensity of the incoming light. This means it is not possible to make a true statement about the relative reflectivity by measuring the intensity alone. The same applies in transmission.

Therefore a signal is now generated by the comparator from the input values by forming a quotient from the respective signals received from the detector 19 and the reference detector 19', i.e. from the reflected radiation on the sample 3 and the incident light radiation, as was detected in the reference region. In this way one obtains a relative signal that is practically constant.

The next signal-processing step involves forming a value for the thickness of the thin layer, or the partial regions of the thin layer 15, e.g. in the form of spots, that is changing due to interaction with species of the sample to be tested. For this purpose, as already described above, there is the calibration table or lookup table stored in a computer in at least one database.

As another signal-processing step, one can consider the effect caused by the liquid used here in the test arrangement and by the species to be analyzed that it contains. To do this, again the calibration table or look up table stored in the computer with the evaluation unit is used. In this way the final, processed measurement result is obtained.

This measurement result is constant over a wide range of incident light intensities, as long as the reflection coefficient derived from them is constant. Thus the measured value results from the measurement of reflection or transmission at (for example) the partial region of the thin layer 15, and then forming the reflection and/or transmission coefficients, unaffected by the intensity or intensity fluctuations.

In the following some general details, i.e. details that apply fundamentally to the inventive measurement setup, will be presented.

In the example embodiment described above, it was shown how the light reflected from the thin layer 15 located on the carrier 13, or the partial regions of this thin layer 15, is recorded via a suitable imaging optics with various, sometimes optional filters and filter functions by a detector or a detector arrangement 19, and processed by the downstream evaluation unit, in each case by an effective further processing of the measured intensities and reference intensities. This facilitates the evaluation and significantly improves its quality.

From the reflection or transmission coefficients formed in a specific, defined narrow wavelength range by the evaluation software using the measured intensities and reference intensities, conclusions can be drawn about the thickness of the thin layer, or the thickness of the partial regions/spots of the thin layer, whose change in layer thickness is observed and detected in this same measurement.

According to the invention, to enable an improved and simplified evaluation with a faster quantitative analysis, the detected intensity is correlated with the corresponding optical layer thickness using a mapping function via, for example, the reflection coefficient in dependence on the employed narrow wavelength range of the LED or a broadband light source by using at least one corresponding filter, so that the intensity can be obtained from a lookup table stored in the computer. This significantly reduces the workload for the measurement and the evaluation of results, while significantly increasing the storage capacity requirement in the evaluation unit, which however does not pose a practical problem.

In the experimental setup described here, the light is radiated approximately vertically onto thin layer 15 located on the carrier 13, or the partial regions of the thin layer 13 in the case of the multi-spot arrangement or the microtiter plate. Alternatively a different, slightly oblique angle of incidence of the light can be used.

The measurements were generally performed in accordance with the basic principles of reflectometric interference spectroscopy, as has now been described repeatedly in the literature. Here the light is radiated into the thin layer 15, not coupled in the carrier, and a multiple reflection is measured, not an evanescent field. The reflectometric interference spectroscopy could not until now be adapted to practical applications and made available in the way proposed here.

Basically photoelectric receivers, preferably CCD elements, for example in the form of a video camera, are used as detectors for the reflected light.

If a microtiter plate is used instead of the carrier 13 in the form of a slide, the use of CCD elements basically has the advantage that several sensors can be provided for each well of the microtiter plate for spatially resolved detection and data acquisition; in the example embodiment as CCD sensors in the form of one-dimensional arrays of CCD line sensors.

It is particularly important that these CCD sensors for each well capture both the light radiation reflected by the capture molecules interacting with the species to be analyzed due to changes in the layer thickness, as well as the underlying pattern of the respective well in the form of the predefined encoding in accordance with PCT/EP2010/002728.

This type of detection results in a very high quality temporal resolution of the changes in the layer thickness.

For the practical implementation of the improved analysis of changes in the layer thickness of the thin layer or partial regions of the thin layer in the form of spots, according to the invention, it is also of considerable importance to be able to quickly and clearly recognize the employed prepared carrier as a genuine original product. Scannable bar codes do not suffice for this.

Only by using the layer thickness analysis according to the invention that is presented here, by forming the reflection and transmission coefficients, with subsequent evaluation via the lookup tables, in combination with a pattern recognition as described in detail in PCT/EP2010/002728, does it become at all possible to distinguish between a genuine original product and a counterfeit. This is a fundamental requirement for biomedical applications and/or applications in the field of homeland security.

Therefore in what follows a brief description shall be given of pattern recognition based on the respective patterns that are also in the lookup table, combined with the layer thickness analysis according to the invention.

The detection of changes in layer thickness in combination with the pattern recognition was carried out in the following variants:

Here the description of the variants is only exemplary and relates by way of example to the use of a microtiter plate with depressions, the cavities or wells. For the floors of the wells have not only the thin layer or partial regions of the thin layer, but are prepared for additional pattern recognition and include capture molecules that interact with the species of a sample to be tested, and which should cause a change in the layer thickness. This twofold preparation—pattern recognition and sample test—requires the presence of defined regions in the floors of the wells that produce no change or only an insignificant change in the measured intensities during scanning of the floors of the wells.

In the following regions patterns can be applied and detected on the surface of the floors of the wells—and accordingly also on planar two-dimensional carriers, such as slides:

Patterns when activating the floors of the wells and/or
Patterns when treating the surface in the form of silanization and/or
Patterns during the reaction with a biopolymer and/or
Patterns when immobilizing the selected, specific capture molecules.

Thus the subsequent measurement is not only used to determine the change in layer thickness due to interaction of the species to be tested in the sample with the thin layer, but also for the identification of the pattern previously applied on the thin layer, which represents a much more stringent requirement.

The said patterns are either applied so that defined partial regions are activated or silanized, or reacted with the biopolymer, or the capture molecules are immobilized in defined partial regions, or so that the pattern structure is transferred to the next transformation step by pattern formation that has already taken place in a preceding step.

If for example already at the beginning only a defined partial region of the surface of the floors of the wells was activated, then only these activated regions can be silanized. The pattern therefore continues. The pattern formation can equally well be done during the conversion step of silanization, by applying a mask, by a specific multi-spot application, or the like. The same applies to each of the conversion steps up to the immobilization of the capture molecules.

The pattern formation described in this simplified manner is used for coding the respective microtiter plate, or likewise for coding the respective planar carrier, for example to distinguish counterfeit products from genuine products, thus providing quality assurance. It should again be noted that this pattern formation and coding as such are not part of the present invention. The present invention has the purpose of recording and evaluating, preferably automatically, at a high standard of quality, the patterns formed in this way together with the change in layer thickness caused by the respective observed interaction.

The light directed to the floors of the wells and reflected from the surface of the thin layer distributed as multi-spots on the floors of the wells, is influenced in very different ways. By the interaction of the sample to be tested with the capture molecules, that form a part of the regions of the thin layer distributed as multi-spots on the floors of the wells, the irradiated light is affected differently than for example in regions that have no capture molecules because they are used for pattern recognition and quality assurance. The light that is reflected in varying degrees of intensity in this way, and optionally also the light of the reference beam path, is then detected by the detector arrangement, which has at least one photodiode. The detector arrangement is again connected with an evaluation unit, as was illustrated using the above example embodiments.

For this the reflected light is detected by scanning from well to well.

By using CCD technology it is possible to associate an individual well with the data acquisition in the respective evaluation unit. The number of scanning and data capture operations corresponds exactly to the number of wells. Here the measured values for the individual wells are captured successively over time.

In contrast to the conventional evaluation of data previously known from reflectometric interference spectroscopy, it is now desirable to detect regions with high intensities and regions where nothing or almost nothing happens, i.e. where no intensity at all or only a very low intensity can be detected.

The detection method that is performed not only on a single well of a microtiter plate, but extended to all the wells, can be simplified by providing a diode scanner line or each row of wells of a microtiter plate. Since for the analysis the capture molecules can be freely assigned in addition to the regions for the pattern recognition, the capture molecules can for example be limited to one row of wells of the microtiter plate or to certain specified rows. This considerably reduces the work needed for the scanning and evaluation, and so also the required storage capacity in the evaluation unit. A steady stream of signals through the respective scanning CCD sensor, the CCD diode, is produced during the scanning, which is easier to process in the evaluation unit.

This simplified embodiment has its limits for interactions between the capture molecules and the species of a sample to be tested, when the interactions are subject to a rapid kinetic process. Because a scan here involves the scanning of an entire row of wells, each scanning CCD sensor must be moved frequently and quickly back and forth, which may shorten the life of the sensor.

For the expert it should be obvious that all the described embodiments can be applied equally well to thin layers on planar carriers, such as slides and microtiter plates.

To increase the reliability of the evaluation process, the required or optional components that were also discussed in the various embodiments, such as the light source and filters, may also be provided with a specific coding. This measure allows one to calibrate the whole measuring system, for example by matching with a lookup table, without significantly increasing the work required. This ensures that the initially measured intensities are mapped correctly. In this way one effectively avoids, for example, incorrect amplitude values.

The invention claimed is:

1. A method for detecting at least one of chemical, biochemical, medical reactions, physical reactions, binding processes, and accretion processes by determining optical properties by measuring intensities on a thin layer having a sample thereon, comprising:
producing light of more than one wavelength in a desired narrow wavelength range from light emitted in a narrow wavelength range or from light emitted in a wide wavelength range and filtered with a filter arrangement,
passing the light having the desired narrow wavelength range through a beam splitter which directs a first part of the light onto the thin layer disposed on an at least partially transparent substrate and a second part of the light onto a reference detector having spatial resolution that measures a current incident light intensity,
irradiating the thin layer with the first part of the light,
simultaneously measuring spatially-resolved interferences on the thin layer over the desired narrow wavelength range using a detector having spatial resolution,
forwarding signals measured by the detector and the reference detector to an evaluation unit, which forms quotients of the signals obtained from the detector and the reference detector for each wavelength of the light and determines therefrom for each image point of the thin layer at least one of reflection and transmission coefficients at the same time and independently of the current incident light intensity and correlates the determined reflection and transmission coefficients with the optical layer thickness at every measured image point stored in at least one database in the evaluation unit to determine qualitatively or quantitatively the optical properties of the thin layer, wherein the at least one database contains all data required to associate each measurement result with a quantitative or quantitative result, and
deriving the optical layer thickness as a change in gray-scale value in the optical properties of the thin layer caused by interacting with species of the sample from a gray-scale value analysis that compares the gray-scale value to an index value in a conversion factor stored in the at least one database.

2. The method of claim 1, wherein the evaluation unit comprises a comparator and a related database in form of at least one lookup table, and wherein the conversion factor is stored in the lookup table.

3. The method of claim 1, wherein the desired narrow wavelength range is selected so as to include wavelengths that produce both maxima and minima in the measured interferences.

4. The method of claim 1, wherein the thin layer is disposed over an entire surface of the substrate.

5. The method of claim 1, wherein the thin layer is disposed over several partial regions on a surface of the substrate.

6. The method of claim 1, wherein the thin layer is disposed over multiple spots on a surface of the substrate.

7. A device for determining optical properties by measuring intensities on a thin layer having a sample thereon, comprising:
at least one light source that produces light of more than one wavelength,
an at least partially transparent substrate having the thin layer disposed at least partially over a surface of the substrate,
a beam splitter which directs a first part of the light onto the thin layer disposed on the at least partially transparent substrate and a second part of the light onto a reference detector having spatial resolution that measures a current spatially-resolved incident light intensity,
a detector having spatial resolution simultaneously measuring spatially-resolved interferences on the thin layer over a desired narrow wavelength range;
a computer connected to both the detector and the reference detector and receiving spatially resolved signals from the detector and the reference detector, said computer comprising a database and comparator that performs a gray-scale value analysis that compares gray-scale value to an index value in a conversion factor stored in the database by correlating reflection or transmission coefficients determined from the measured interferences with previously known information and distribution functions so as to determine the optical properties of the thin layer by way of correlation with a conversion factor, wherein the computer derives an optical layer thickness of the thin layer as a change in gray-scale value in the optical properties caused by interacting with species of the sample from the gray-scale value analysis.

8. The device of claim 7, wherein the light source comprises a high-power LED or a laser diode.

9. The device of claim 7, wherein the light source is coupled with at least one wavelength-selective filter to select a narrow-band wavelength range.

10. The device of claim 7, wherein the detector is formed as a one-dimensional CCD sensor, a CCD array, or a two-dimension I CCD sensor in form of a CCD image sensor.

11. The device of claim 7, wherein the reference detector is formed as a one-dimensional CCD sensor, a CCD array, or a two-dimensional CCD sensor in form of a CCD image sensor.

12. The device of claim 7, wherein the substrate is constructed as a microtiter plate.

* * * * *